United States Patent [19]

Gesson et al.

[11] Patent Number: 4,731,468

[45] Date of Patent: Mar. 15, 1988

[54] AGLYCONS

[75] Inventors: Jean-Pierre Gesson, Chasseneuil du Poitou; Martine Mondon, Poitiers, both of France; Abdallah A. Abdallah, Omdurman,

[73] Assignee: Laboratoires Hoechst S.A., France

[21] Appl. No.: 645,360

[22] Filed: Aug. 29, 1984

[30] Foreign Application Priority Data

Aug. 30, 1983 [FR] France ............................. 83 13877

[51] Int. Cl.$^4$ ..................... C07C 57/02; C07C 49/115
[52] U.S. Cl. ................................... 560/255; 568/326; 536/6.4
[58] Field of Search .......................... 514/34; 536/6.4; 568/326; 560/255

[56] References Cited

U.S. PATENT DOCUMENTS 4,418,192 11/1983 Tanaka et al. ...................... 536/6.4
4,465,671 8/1984 Angelucci et al. .................. 514/34

FOREIGN PATENT DOCUMENTS 0049403 4/1982 European Pat. Off. .
2506772 12/1982 France .

OTHER PUBLICATIONS

The Journal of Organic Chemistry, vol. 48 (8):1328-1333 (Jun. 1982) Aklavin-Type Anthracyclinones: Brief, Regiospecific Syntheses of Tetracyclic Intermedicates by Frank M. Hauser et al.
Chemical Abstracts, vol. 101; Abstract No. 103524 q, "One-electron Reduction of Variously Substituted Anthraquinones", by A. Anne et al.
The Journal of Organic Chemistry, vol. 46 (13):2798-2804 (Jun. 19, 1981), Phenyl Selenide Anion, A Superior Reagent for the $S_n2$ Cleavage of Esters and Lactones, by Dennis Liotta et al.
The Journal of Antibiotics, vol. XXXIV (12):1596-1607 (Dec. 1981) Structure-Activity Relationships of Anthracyclines Relative to Cytotoxicity and Effects on Macromolecular Synthesis in L1210 Leukemia Cells by Matsuzawa (and Oki) et al. (4 authors).
Tetrahedron Letters, vol. 21 (35):3351-3354 (1980), A General Route to 11-Deoxyanthracyclines by J. P. Gesson et al.
Tetrahedron Letters, vol. 21 (18):4777-4780 (1980), The Vinyl Ketone Acetal Route to Aklavinone and 11-Deoxydaunomycinone by J. G. Bauman et al.
Tetrahedron Letters, vol. 22 (18):1667-1670 (1981), A Regiospecific Approach to 6-Deoxyanthracyclinones; The Structure of γ-citromycinone by Andrew S. Kende et al.
J. Chem. Soc. Chem. Commun., 421-23 (1982) by Jean-Pierre Gesson et al., Total Synthesis of 11-Deoxydaunomycinone.

Primary Examiner—Anton H. Sutto
Attorney, Agent, or Firm—Finnegan, Henderson, Farabow, Garrett & Dunner

[57] ABSTRACT

The present invention relates to new aglycons which correspond to the general formula:

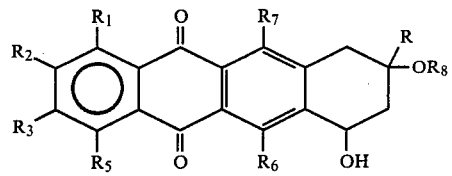

in which:

$R_1$, $R_2$, $R_3$ and $R_5$, which can be identical or different, represent a hydrogen atom or a group OH, OMetal or $OR_4$, $R_4$ being a substituted or unsubstituted $C_1$ to $C_6$ alkyl group, R represents a hydrogen atom or a group $COCH_2R'$, R' being hydrogen or an alkyl, hydroxyl, alkoxy or aryl group, $R_6$ and $R_7$, which are always different, represent either a hydrogen atom or an OH group, and $R_8$ represents a hydrogen atom or the group $CH_3CO$—.

Application to the preparation of antibiotics and antitumoral agents.

7 Claims, No Drawings

AGLYCONS

The present invention relates to new aglycons useful for the preparation of antibiotics and antitumoral agents of the anthracyclin series, and to processes for their preparation.

The anthracyclins represented by the general formula (I) below:

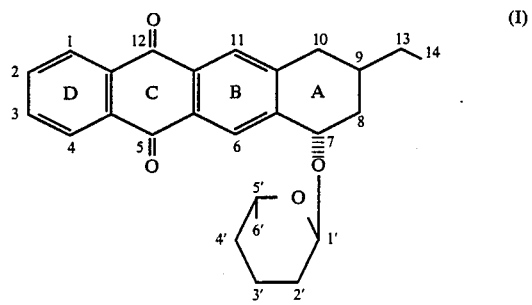

constitute an important family of antibiotics and antitumoral agents. Certain members of this family (for example daunorubicin and doxorubicin) are successfully used clinically for the treatment of various forms of cancer (acute leukemia, breast cancer, cancer of the urinary tract, Hodgkin's disease, etc.).

Their remarkable cytotoxic activity is nevertheless limited by adverse side-effects and in particular by significant cardiotoxicity. As this is related to the dose of antibiotic used, it necessitates the irreversible interruption of the treatment beyond a certain threshold.

Numerous attempts have therefore been made in recent years to improve the therapeutic index of these compounds: a reduction in the cardiotoxicity appears to be more important than an increase in their weight efficacy.

The modifications made concern the aglycon and/or the sugar by total synthesis, by biosynthesis or by hemisynthesis.

The modifications made concern all the rings (A-B-C-D) and also the sugar. The products obtained are generally classed in various categories according to the substitution of the B ring:

I—Derivatives dihydroxylated in the 6-position and 11-position (this category includes daunorubicin-Compound II—and doxorubicin'Compound III).

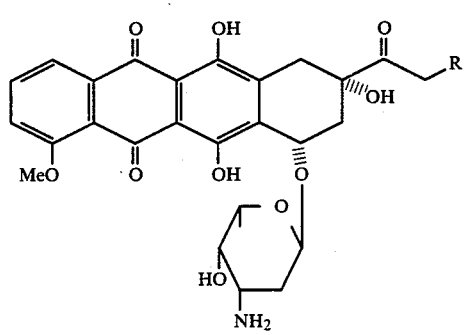

Compound (II) = R = H
Comound (III) = R = OH

DAUNORUBICIN (II): discovered simultaneously in Italy (Farmitalia) and in France (Rhône-Poulenc).

DOXORUBICIN (III): isolated from *Streptomyces peucetius* var. caesius in 1969 (Farmitalia).

II—Derivatives monohydroxylated in the 6-position (11-deoxy series).

(III)—Derivatives monohydroxylated in the 11-position (6-deoxy series).

I—EXAMPLES OF DERIVATIVES DIHYDROXYLATED IN THE 6-POSITION AND 11-POSITION

1. Attempts to modify the D ring

The analogs of the compounds II and III demethoxylated in the 4-position have been prepared and have a higher therapeutic index than the natural compounds (F. ARCAMONE, Anticancer Antiobiotics, Academic Press, 1981, chapter 7). Furthermore, various substituents have been introduced: in the 1-position and 4-position (Cl, CH$_3$) or 2-position and 3-position (Cl, CH$_3$ or benzo) (cf. F. ARCAMONE et al. Experientia 34, 1255, 1978).

The aromatic D ring has been replaced by an aromatic sulfur heterocycle (A. S. KENDE and H. NEWMAN, European Patent Application No. 17,469, 15th Oct. 1980).

2. Attempts to modify the C ring

Relatively few have been made. However, the preparation of 5-iminodaunorubicin must be mentioned (L. TONG, D. W. HENRY and E. M. ACTON, J. Med. Chem., 22, 36 (1979)).

3. Attempts to modify the A ring

Numerous analogs have been prepared, most frequently by means of hemisynthesis by conversion of the natural products: derivatives with OCH$_3$ in the 10-position or 8-position, 9-deoxy analogs (with or without Δ-9 double bond), compounds with modified side-chains (9-deacyl), reduced products and derivatives of the carbonyl in the 13-position (cf. F. ARCAMONE, Anticancer Antibiotics, op. cit.).

4. Attempts to modify the sugar

Modifications have been made to all the positions (1', 2', 3', 4', 5', 6') of the pyranose ring and the "in vivo" antitumoral activity has frequently been preserved or even improved.

II—EXAMPLE OF DERIVATIVES MONOHYDROXYLATED IN THE 6-POSITION
(11-deoxy series)

11-Deoxydaunorubicin and 11-deoxydoxorubicin were obtained by Farmitalia in 1980 by fermentation. They have an "in vivo" antitumoral activity similar to that of compounds (II) and (III) at larger doses, but with a lower toxicity.

Numerous total syntheses of the corresponding aglycons have been described (cf., in particular, J. P. GESSON and M. MONDON, Chem. Comm., 1982, 421), as has that of 4-demethoxy-11-deoxydaunorubicin and 4-demethoxy-11-deoxydoxorubicin (H. UMEZAWA et al., J. of Antibiotics 33, 1581 (1980)).

It should also be pointed out that natural compounds of the anthracyclin family exist which do not possess a hydroxyl in the 11-position: aclacinomycins, pyrromycins, cinerubins, etc.

III—EXAMPLE OF DERIVATIVES MONOHYDROXYLATED IN THE 11-POSITION
(6-deoxy series)

Some natural anthracyclins are known which do not possess a hydroxyl in the 6-position: α-citromycin, α$_2$-rhodomycin.

On the other hand, 6-deoxydaunorubicin and 6-deoxydoxorubicin have not yet been isolated or synthesized.

In a recent publication (J. Org. Chem., 48, 405, 1983), F. ARCAMONE et al. describe the synthesis of 4-demethoxy-6-deoxydaunorubicin, for which the first in vitro tests (HeLa cells) show a cytotoxicity similar to that of daunorubicin.

The mode of action of all these molecules is probably complex. It is acknowledged that it involves an insertion into the DNA chain, which is a favorable process because of the partial inherent flatness of the tetracyclic system.

The molecule then undergoes reduction, leading to an intermediate radical ion which would cause the formation of toxic entities (for example: HO·, $H_2O_2$) in the tissues and then the formation of a reduced form of the quinone system. This form would be responsible for the elimination of the sugar and the formation of free aglycon (without the oxygen-containing group in the 7-position).

These considerations led HANSCH et al. (Il Farmaco 35, 12, 965 (1980)) to suggest the introduction of small donor groups (OH, OCH$_3$) into the 2-position or 3-position.

In fact, it may be considered that, by modifying the redox potential of the quinone system, the introduction of various substituents into the D ring could restrict these various reactions and lead to compounds with a higher therapeutic index. This entails the synthesis of new compounds by a large number of researchers and involves looking for a possible correlation between the redox potential and/or the antitumoral activity and/or the toxicity.

Firstly by studying and examining all these results obtained by the different researchers, and secondly by noting that:

1°—in the 11-deoxy series, all other things being equal, certain natural compounds having a hydroxyl in the 1-position have a more pronounced antitumoral activity than the compounds not hydroxylated in the same position (example: relative activities of cinerubin A and aclacinomycin A) (ref. S. T. CROOK and S. D. REICH, Anthracyclins, Academic Press, 1980, Chapter 6), and 2°—the process for the reductive elimination of L-daunosamine is definitely accelerated by the presence of the phenol in the peri position, by analogy with the rapid and selective hydrogenolysis of a benzyl alcohol group in the 10-position in α-citromycinone,

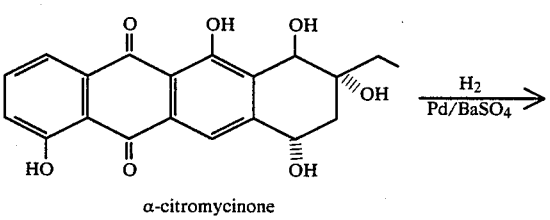

α-citromycinone

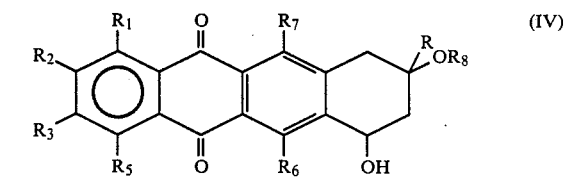

γ-citromycinone the Applicant Company has been able to synthesize a whole series of compounds—aglycons—capable of providing very active drugs of low toxicity.

The present invention relates to new aglycons useful for the preparation of antibiotics and antitumoral agents, which correspond to the general formula IV below:

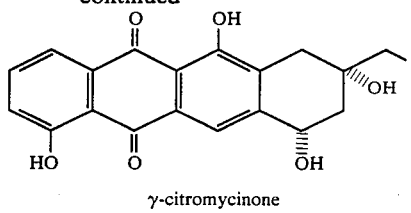

(IV)

in which:

R$_1$, R$_2$, R$_3$ and R$_5$, which can be identical or different, represent a hydrogen atom or a group OH, OMetal or OR$_4$, R$_4$ being a substituted or unsubstituted C$_1$ to C$_6$ alkyl group, R represents a hydrogen atom or a group COCH$_2$R', R' being hydrogen or an alkyl, hydroxyl, alkoxy or aryl group, R$_6$ and R$_7$, which are always different, represent either a hydrogen atom or an OH group, and R$_8$ represents a hydrogen atom or the group CH$_3$CO—, with the proviso that:

1°—R$_1$, R$_2$ and R$_3$ are never simultaneously hydrogen when R$_7$ and R$_8$ represent the hydrogen atom and R is the group COCH$_2$R', and 2°—if R$_1$, R$_2$, R$_3$ and R$_6$ are hydrogen, R$_5$ is other than hydrogen and OCH$_3$.

According to the invention, the two OH groups of the A ring are in the cis or trans position relative to one another.

In an advantageous embodiment of the subject of the invention, the products obtained are 11-deoxyaglycons.

In another advantageous embodiment of the subject of the invention, the products obtained are 6-deoxyaglycons.

According to the invention, the 11-deoxyaglycons are taken from the group comprising:
the aglycon in which R$_1$=OH; R$_2$=R$_3$=R$_5$=H; R$_6$=OH; R=COCH$_3$; R$_8$=H,
the aglycon in which R$_1$=R$_3$=R$_5$=H; R$_2$=OCH$_3$; R$_6$=OH; R=COCH$_3$; R$_8$=H,
the aglycon in which R$_1$=R$_2$=R$_5$=H; R$_3$=OCH$_3$; R$_6$=OH; R=COCH$_3$; R$_8$=H and
the aglycon in which R$_1$=R$_2$=R$_3$=R$_5$=R=H; R$_6$=OH; R$_8$=COCH$_3$.

In an advantageous embodiment of the subject of the invention, the 6-deoxyaglycon corresponds to the product in which: R$_1$=R$_2$=R$_3$=R$_6$=H; R$_7$=OH; R$_5$=OH; R=COCH$_3$.

The present invention also relates to a process for the preparation of the 11-deoxyaglycons according to the present invention, which process comprises the following steps:

1st step: Preparation of the enol ether of the general formula V

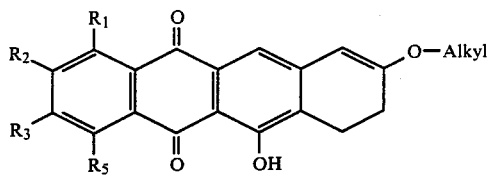

$R_1$, $R_2$, $R_3$ and $R_5$ having the same meanings as above, by reaction of a halogenated naphthoquinone of the general formula VI with a diene of the general formula VII

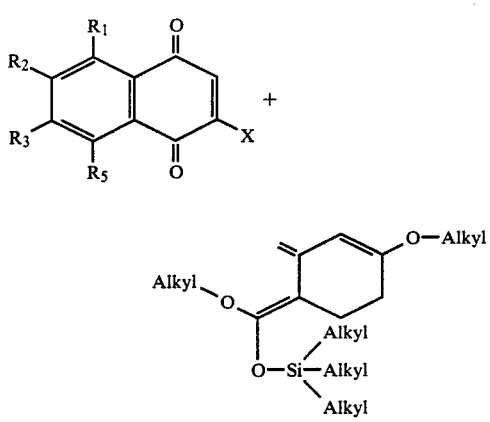

$R_1$, $R_2$, $R_3$ and $R_5$ having the same meanings as above and X representing a halogen atom.

2nd step: Hydrolysis of the enol ether V to the corresponding ketone of the general formula VIII

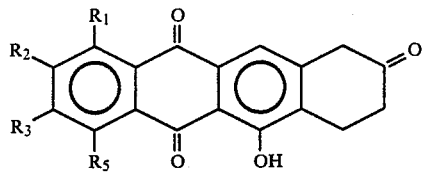

3rd step: Ethynylation of the ketone VIII to the corresponding product of the formula IX

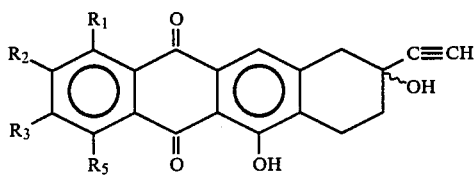

followed by hydration to the product of the general formula X

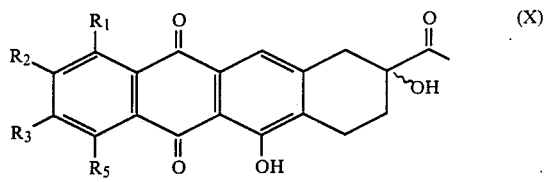

4th step: Bromination on the benzyl carbon, followed by basic hydrolysis, to give the desired product The present invention also relates to a process for the preparation of the 6-deoxyaglycons according to the present invention, which process comprises using a diene of the general formula XI

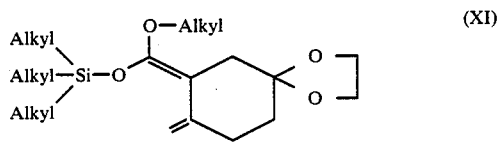

in the 1st step, the other steps being similar to the process described for the 11-deoxy derivatives.

In addition to the abovementioned provisions, the invention also comprises other provisions which will become apparent from the description which now follows with reference to examples for the preparation of products according to the present invention. It must be clearly understood, however, that these examples are given solely by way of illustration of the subject of the invention and in no way imply a limitation.

EXAMPLE 1

PREPARATION OF 5-HYDROXY-8-METHOXY-3,4-DIHYDRO-1H-NAPHTHACENE-2,6,11-TRIONE

A solution of the keten acetal VII (2.5 g; 8.9 mmol) in tetrahydrofuran (THF) (3 ml) is added dropwise at 0° C. to a solution of 3-chloro-6-methoxy-1,4-naphthoquinone (1.9 g; 8.6 mmol) in THF (20 ml). The reaction medium is stirred overnight at ambient temperature. After evaporation of the solvent, the solid obtained is added slowly to a solution of HF (25 ml)-SbF$_5$ (5 ml) at −40° C. in a Teflon flask. The mixture is kept at −40° C. for 20 minutes and then poured slowly into 500 ml of a water/ice mixture. After extraction with methylene chloride, the organic phase is washed with water, dried over sodium sulfate and then evaporated. The tetracyclic ketone is purified by chromatography under pressure (eluent: CH$_2$Cl$_2$) (1.11 g; 40%).

EXAMPLE 2

PREPARATION OF (±)-2,5-DIHYDROXY-2-ETHYNYL-8-METHOXY-1,2,3,4-TETRAHYDRONAPHTHACENE-6,11-DIONE

Acetylene, purified by passing first through a trap cooled with ice and then through a trap containing concentrated sulfuric acid, is bubbled through 40 ml of anhydrous THF for 1 hour. Ethylmagnesium bromide (40 ml, 1M in THF, 40 mmol) is then added dropwise. After the addition, the solution is evaporated under reduced pressure and the residue is taken up with 80 ml of methylene chloride (CH$_2$Cl$_2$) distilled over P$_2$O$_5$.

The ketone prepared in Example 1 (386 mg; 1.2 mmol), dissolved in $CH_2Cl_2$ (150 ml), is added dropwise to this solution, cooled to $-40°$ C. The reaction mixture is stirred for 1 hour at between $-40°$ C. and $-20°$ C., then hydrolyzed with a 0.1N solution of hydrochloric acid and then extracted in the conventional manner with methylene chloride. Chromatography under pressure ($CH_2Cl_2$) makes it possible to separate the unreacted starting ketone (148 mg; 38%) from the ethynylcarbinol formed (165 mg; 43%).

EXAMPLE 3

PREPARATION OF (±)-4-DEMETHOXY-7,11-DIDEOXY-3-METHOXYDAUNOMYCINONE

Amberlite IRN-77 resin is treated with mercuric oxide, HgO, in the following manner: the resin (50 g) is suspended in a dilute solution of $H_2SO_4$ and then washed several times with water by decantation. A solution of mercuric oxide (0.5 g) in 1 liter of dilute sulfuric acid is then added to the resin. The resin is washed again with water and then dried under reduced pressure.

A mixture of ethynylcarbinol prepared as indicated in Example 2 (140 mg; 0.4 mmol) and of resin treated with HgO (2 g), in 200 ml of ethanol and 40 ml of water, is heated under reflux for 16 hours. The cooled reaction mixture is filtered. The filtrate is extracted with methylene chloride. The organic phase is washed with water and dried over sodium sulfate. Evaporation of the methylene chloride under reduced pressure gives the hydroxyketone (145 mg; 98%), which is used without subsequent purification.

EXAMPLE 4

PREPARATION OF (±)-4-DEMETHOXY-11-DEOXY-3-METHOXYDAUNOMYCINONE

A solution, placed under nitrogen, of hydroxyketone×(100 mg; 0.27 mmol) and epoxycyclohexane (132 mg; 1.35 mmol) in 250 ml of $CCl_4$ and 50 ml of $CH_2Cl_2$ is irradiated with a 60 W lamp while a solution of bromine in $CCl_4$ (0.36 ml of a 0.1M solution diluted in 50 ml of $CCl_4$) is added dropwise. After the addition, the solution is stirred for 30 minutes and then concentrated under reduced pressure. The reaction medium is taken up with 60 ml of acetone. A solution of calcium hydroxide, obtained from calcium oxide (48 mg of CaO, 0.82 mmol, in 50 ml of water), is added to the solution. The violet reaction mixture is stirred for 30 minutes and then neutralized with a saturated solution of oxalic acid and extracted in the conventional manner with methylene chloride. Chromatography under pressure ($CH_2Cl_2$/MeOH, 99/1) makes it possible to separate the (±)-4-demethoxy-11-deoxy-3-methoxydaunomycinone (37.2 mg; 36%) from the (±)-7-epi-4-demethoxy-11-deoxy-3-methoxydaunomycinone (43.8 mg; 42.5%).

EXAMPLE 5

PREPARATION OF (±)-2-(1,1-ETHYLENEDIOXYETHYL)-2,7,12-TRIHYDROXY-1,2,3,4-TETRAHYDRONAPHTHACENE-6,11-DIONE

A solution of (±)-2-acetyl-2,7,12-trihydroxy-1,2,3,4-tetrahydronaphthacene-6,11-dione (740 mg; 2.1 mmol) and ethylene glycol (280 mg; 4.4 mmol) in 400 ml of benzene, in the presence of a catalytic quantity of para-toluenesulfonic acid, is heated under reflux for 12 hours in a 500 ml round-bottomed flask. The flask is equipped with a "Dean Stark" apparatus (making it possible to remove the water formed as an azeotrope with benzene).

After washing with water and drying over sodium sulfate, the organic phase is evaporated to give the dioxolan (816 mg; 98%).

EXAMPLE 6

PREPARATION OF (±)-4-DEMETHOXY-6-DEOXY-4-HYDROXYDAUNOMYCINONE

A solution of bromine (8 ml of a 0.1M solution; 0.8 mmol) is added at 45° C. to a solution of dioxolan obtained as indicated in Example 5 (260 mg; 0.66 mmol), epoxycyclohexane (324 mg; 3.3 mmol) and azobisisobutyronitrile (30 mg; 0.18 mmol) in 400 ml of $CCl_4$. The solution is kept at the same temperature for 3 hours and then concentrated under reduced pressure. The reaction medium is taken up with a solution consisting of THF and 0.5N sodium hydroxide solution (1:1), and the mixture is stirred overnight at ambient temperature. After neutralization with 0.1N HCl and conventional extraction with methylene chloride, the crude reaction mixture is taken up with a solution of $CF_3COOH$ (20 ml)-$H_2O$ (4 ml) cooled to 0° C., and stirred for 4 hours at this temperature. The solution is poured all at once into 200 ml of a water/ice mixture and extracted with methylene chloride.

The resulting aglycon (66 mg; 28%)

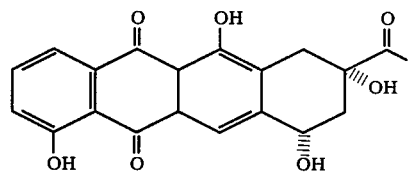

is purified by thin layer chromatography ($CH_2Cl_2$/MeOH; 98/2).

EXAMPLE 7

PREPARATION OF (±)-4-DEMETHOXY-9-DEACETYL-7,11-DIDEOXYDAUNOMYCINONE

Sodium cyanoborohydride (6.2 g; 102 mmol) is added slowly to a solution of tetracyclic ketone VIII (3 g; 10.2 mmol) in 900 ml of THF and 90 ml of water. Throughout the addition, the reaction medium is kept at a pH of 2–3 by the addition of a 1N solution of hydrochloric acid. The solution is stirred for a further 30 minutes and then extracted with methylene chloride. The organic phase is washed with water, dried over sodium sulfate and evaporated under reduced pressure to give the corresponding alcohol (2.95 g; 98%), which does not require subsequent purification.

EXAMPLE 8

PREPARATION OF (±)-9-O-ACETYL-4-DEMETHOXY-9-DEACETYL-7,11-DIDEOXYDAUNOMYCINONE

A solution of the alcohol obtained as indicated in Example 7 (470 mg; 1.6 mmol), in 15 ml of acetic anhydride and 30 ml of pyridine, is stirred for 16 hours at −10° C. The reaction medium is poured into a water-/ice mixture and extracted with methylene chloride. The organic phase is washed with a 1N solution of hydrochloric acid and then with water and dried over sodium sulfate. The solvent is evaporated off under reduced pressure. Chromatography of the residue under pressure (eluent: CH$_2$Cl$_2$) makes it possible to separate the acetate (430 mg; 80%) from the diacetate formed (54 mg; 9%) and from the starting alcohol (24 mg; 5%).

EXAMPLE 9

PREPARATION OF (±)-9-O-ACETYL-4-DEMETHOXY-9-DEACETYL-11-DEOXYDAUNOMYCINONE

A solution of the previous compound (145 mg; 0.43 mmol) in 700 ml of CCl$_4$, placed under nitrogen and in the presence of epoxycyclohexane (216 mg; 2.2 mmol), is irradiated with a 60 W lamp while a solution of bromine in CCl$_4$ (4.8 ml of a 0.1M solution diluted in 70 ml of CCl$_4$) is added dropwise. After the addition, the solution is stirred for 30 minutes and then concentrated under reduced pressure. The reaction medium is taken up with 100 ml of THF and 50 ml of 0.1N hydrochloric acid, stirred at ordinary temperature for 1 hour 30 minutes and then extracted with methylene chloride in a conventional manner.

Chromatography of the crude product under pressure (eluent: CH$_2$Cl$_2$) makes it possible to separate the (±)-9-O-acetyl-4-demethoxy-9-deacetyl-11-deoxydaunomycinone (43 mg; 28%) from the (±)-7-epi-9-O-acetyl-4-demethoxy-9-deacetyl-11-deoxydaunomycinone (74 mg; 49%).

CHARACTERISTICS OF THE PRODUCTS OBTAINED

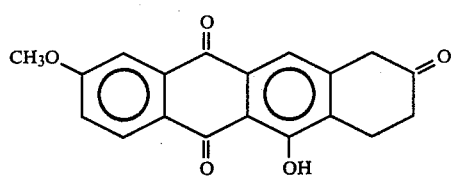

5-Hydroxy-9-methoxy-3,4-dihydro-1H-naphthacene-2,6,11-trione

Yield: 40%.

Melting point: 232°–234° C.

M.S.: m/z=322(96%), 294(75%), 293(67%), 280(100%).

I.R. (KBr disc): 2960 cm$^{-1}$, 1710, 1670, 1630, 1590, 1570, 1490, 1470, 1430, 1420, 1370, 1345, 1310, 1295, 1280, 1230, 1170, 1110, 1085, 1060, 1030, 1000, 960.

NMR (CDCl$_3$): 2.6 ppm (triplet, J=7 Hz, 2H); 3.27 (triplet, J=7 Hz, 2H); 3.68 (singlet, 2H); 3.98 (singlet, 3H); 7.23 (doublet of doublets, J=7 Hz and 2 Hz, 1H); 7.53 (singlet, 1H); 7.68 (doublet, J=2 Hz, 1H); 8.20 (doublet, J=7 Hz, 1H); 13.1 (singlet, 1H).

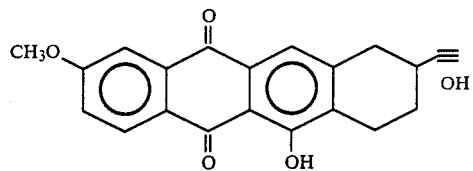

(±)-2,5-Dihydroxy-2-ethynyl-9-methoxy-1,2,3,4-tetrahydronaphthacene-6,11-dione

Yield: 50%.

Decomposition T°: 230° C.

M.S.: m/z=348(57%), 330(70%), 322(57%), 280(100%).

I.R. (KBr disc): 3530 cm$^{-1}$, 3440, 3290, 3240, 2960, 1670, 1630, 1600, 1470, 1430, 1380, 1370, 1340, 1295, 1270, 1230, 1200, 1090, 1020, 1010, 980, 940, 850, 820, 800, 750.

NMR (CDCl$_3$): 2.16 ppm (triplet, J=7 Hz, 2H); 2.47 (singlet, 1H); 3.22 (singlet, 2H); 3.03 (triplet, J=7 Hz, 2H); 3.99 (singlet, 3H); 7.24 (doublet of doublets, J=7 Hz and 2 Hz, 1H); 7.54 (singlet, 1H); 7.69 (doublet, J=2 Hz, 1H); 8.20 (doublet, J=7 Hz, 1H); 13.15 (singlet, 1H).

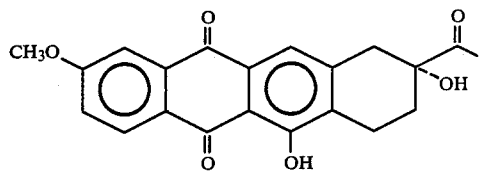

(±)-2-Acetyl-2,5-dihydroxy-9-methoxy-1,2,3,4-tetrahydronaphthacene-6,11-dione (±)-4-Demethoxy-7,11-dideoxy-2-methoxydaunomycinone Yield: 98%.

Melting point: 244°–246° C.

M.S.: m/z=366(10%), 348(6%), 323(100%), 305(33%), 293(25%), 280(18%).

I.R. (KBr disc): 3600 cm$^{-1}$ (fine), 2965, 1715, 1670, 1630, 1595, 1570, 1500, 1470, 1460, 1450, 1425, 1410, 1390, 1360, 1350, 1340, 1300, 1270, 1250, 1230, 1200, 1175, 1105, 1090, 1060, 1040, 1025, 990, 960, 940, 920, 895, 880, 850, 815, 795, 780, 770, 750, 720, 680, 630, 610.

NMR (CDCl$_3$): 2.02 ppm (multiplet, 2H); 2.37 (singlet, 3H); 3.12 (multiplet, 4H); 3.99 (singlet, 3H); 7.25 (doublet of doublets, J=7 Hz and 2 Hz, 1H); 7.58 (singlet, 1H); 7.71 (doublet, J=2 Hz, 1H); 8.20 (doublet, J=7 Hz, 1H); 13.18 (singlet, 1H).

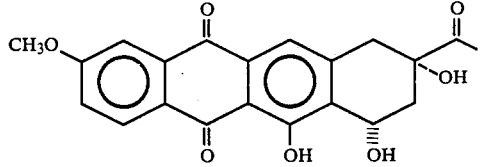

(±)-2-Acetyl-9-methoxy-2α,4α,5-trihydroxy-1,2,3,4-tetrahydronaphthacene-6,11-dione (±)-4-Demethoxy-11-deoxy-2-methoxydaunomycinone Yield: 35%.
Melting point: 220°-223° C.
M.S.: m/z=382(15%), 346(100%), 331(66%), 321(49%), 293(30%), 247(22%).
I.R. (KBr disc): 3250 cm⁻¹ (broad), 2960, 1715, 1670, 1630, 1595, 1500, 1475, 1440, 1390, 1370, 1350, 1340, 1320, 1300, 1270, 1230, 1215, 1205, 1175, 1125, 1105, 1085, 1060, 1040, 1030, 1005, 985, 930, 910, 900, 870, 850, 830, 810, 785, 775, 750, 740, 730, 635.
NMR (CDCl₃): 2.28 ppm (2H); 2.42 (singlet, 3H); 3.06 (singlet, 1H); 3.18 (singlet, 1H); 4.00 (singlet, 3H); 4.58 (1H); 5.30 (multiplet, W₁=8.5 Hz, 1H); 7.26 (doublet of doublets, J=7 Hz and 2 Hz, 1H); 7.63 (singlet, 1H); 7.70 (doublet, J=2 Hz, 1H); 8.26 (doublet, J=7 Hz, 1H); 13.43 (singlet, 1H).

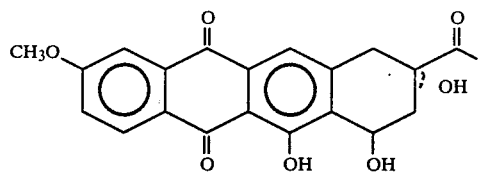

(±)-2-Acetyl-9-methoxy-2α,4β,5-trihydroxy-1,2,3,4-tetrahydronaphthacene-6,11-dione (±)-7-Epi-4-demethoxy-11-deoxy-2-methoxydaunomycinone Yield: 34%.
Melting point: 203°-204° C.
M.S.: m/z=382(15%), 346(65%), 321(100%), 293(58%), 268(20%).
I.R. (KBr disc): 3250 cm⁻¹ (broad), 2970, 2930, 1710, 1670, 1630, 1595, 1570, 1500, 1470, 1425, 1390, 1360, 1340, 1300, 1280, 1230, 1200, 1100, 1070, 1025, 985, 820.
NMR (CDCl₃): 2.39 ppm (singlet, 3H); 3.99 (singlet, 3H); 5.41 (broad triplet, W₁=20 Hz); 7.25 (doublet of doublets, J=7 Hz and 2 Hz, 1H); 7.59 (singlet, 1H); 7.72 (doublet, J=2 Hz, 1H); 8.25 (doublet, J=7 Hz, 1H); 13.68 (singlet, 1H).

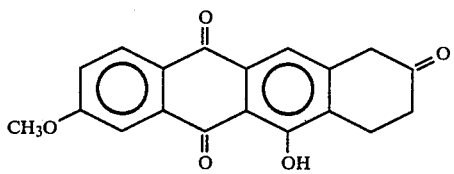

5-Hydroxy-8-methoxy-3,4-dihydro-1H-naphthacene-2,6,11-trione

Yield: 40%.
Melting point: 248°-250° C.
M.S.: m/z=322(73%), 294(39%), 293(24%), 280(100%).
I.R. (KBr disc): 2970 cm⁻¹, 1710, 1660, 1620, 1590, 1570, 1490, 1455, 1450, 1430, 1415, 1375, 1340, 1290, 1260, 1230, 1190, 1150, 1075, 1020, 1000, 915, 875, 860, 845, 820, 770, 750, 740, 680, 650, 630.
NMR (CDCl₃): 2.6 ppm (triplet, J=7 Hz, 2H); 3.25 (triplet, J=7 Hz, 2H); 3.68 (singlet, 2H); 3.98 (singlet, 3H); 7.25 (doublet of doublets, J=7 Hz and 2 Hz, 1H); 7.53 (singlet, 1H); 7.70 (doublet, J=7 Hz, 1H); 8.20 (doublet, J=7 Hz, 1H); 12.93 (singlet, 1H).

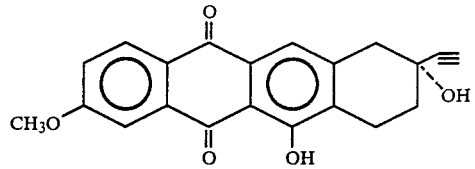

(±)-2,5-Dihydroxy-2-ethynyl-8-methoxy-1,2,3,4-tetrahycronaphthacene-6,11-dione

Yield: 43%.
Melting point: 230°-231° C.
M.S.: m/z=348(73%), 330(99%), 280(100%).
I.R. (KBr disc): 3600 cm⁻¹ (broad), 3260, 2975, 2930, 1670, 1630, 1595, 1570, 1500, 1470, 1430, 1420, 1390, 1350, 1530, 1320, 1300, 1280, 1240, 1170, 1100, 1090, 1050, 1025, 1010, 990, 970, 930, 910, 860, 850, 840, 810, 785, 770, 755, 690.
NMR (CDCl₃): 2.17 ppm (triplet, J=7 Hz, 2H); 2.49 (singlet, 1H); 3.22 (singlet, 2H); 3.08 (triplet, J=7 Hz, 2H); 3.99 (singlet, 3H); 7.27 (doublet of doublets, J=7 Hz and 2 Hz, 1H); 7.54 (singlet, 1H); 7.72 (doublet, J=2 Hz, 1H); 8.22 (doublet, J=7 Hz, 1H); 12.97 (singlet, 1H).

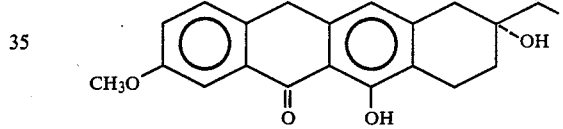

(±)-2-Acetyl-2,5-dihydroxy-8-methoxy-1,2,3,4-tetrahydronaphthacene-6,11-dione (±)-4-Demethoxy-7,11-dideoxy-3-methoxydaunomycinone Yield: 98%.
Melting point: 208°-210° C.
M.S.: m/z=366(8%), 343(4%), 323(100%), 305(25%), 293(16%), 280(12%).
I.R. (KBr disc): 3500 cm⁻¹, 3060, 2960, 1700, 1660, 1630, 1590, 1560, 1540, 1480, 1420, 1380, 1350, 1340, 1330, 1290, 1275, 1240, 1200, 1160, 1105, 1080, 1030, 1000, 990, 980, 950, 925, 910, 895, 860, 850, 825, 810, 800, 770, 750, 720, 710, 630.
NMR (CDCl₃): 2.02 ppm (triplet, 2H); 2.37 (singlet, 3H); 3.07 (multiplet, 4H); 3.99 (singlet, 3H); 7.26 (doublet of doublets, J=7 Hz, 1H); 7.54 (singlet, 1H); 7.72 (doublet, J=2 Hz, 1H); 8.23 (doublet, J=7 Hz, 1H); 12.99 (singlet, 1H).

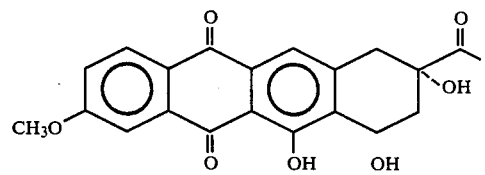

(±)-2-Acetyl-8-methoxy-2α,4α,5-trihydroxy-1,2,3,4-tetrahydronaphthacene-6,11-dione (±)-4-Demethoxy-11-deoxy-3-methoxydaunomycinone Yield: 36%.
Melting point: 222°–223° C.
M.S.: m/z=382(15%), 346(100%), 331(66%), 321(49%), 293(30%), 247(22%).
I.R. (KBr disc): 3540 cm$^{-1}$, 2980, 2970, 1700, 1660, 1630, 1590, 1570, 1450, 1420, 1380, 1350, 1330, 1310, 1300, 1280, 1250, 1240, 1200, 1160, 1120, 1105, 1100, 1080, 1020, 1010, 990, 970, 930, 900, 880, 840, 820, 800, 770, 760, 630.
NMR (CDCl$_3$): 2.28 ppm (multiplet, 2H); 2.41 (singlet, 3H); 4.00 (singlet, 3H); 5.23 (multiplet, W$_{\frac{1}{2}}$=10 Hz, 1H); 7.25 (doublet of doublets, J=7 Hz and 2 Hz, 1H); 7.61 (singlet, 1H); 7.70 (doublet, J=2 Hz, 1H); 8.26 doublet, J=7 Hz, 1H); 13.19 (singlet, 1H).

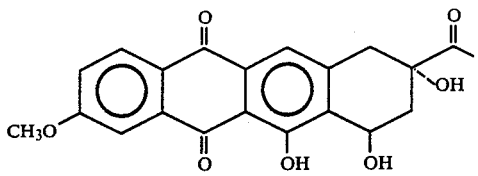

(±)-2-Acetyl-8-methoxy-2α,4β,5-trihydroxy-1,2,3,4-tetrahydronaphthacene-6,11-dione (±)-7-Epi-4-demethoxy-11-deoxy-3-methoxydaunomycinone@

Yield: 42.5%.
M.S.: m/z=382(11%), 346(100%), 321(97%), 293(50%), 268(16%), 247(21%).
I.R. (KBr disc): 3490 cm$^{-1}$ (broad), 2960, 2930, 1720, 1670, 1640, 1600, 1430, 1390, 1360, 1340, 1290, 1240, 1170, 1105, 1095, 1040, 1020, 910.
NMR (CDCl$_3$): 2.40 ppm (singlet, 3H); 4.00 (singlet, 3H); 5.43 (broad triplet, W$_{\frac{1}{2}}$=20 Hz, 1H); 7.25 (doublet of doublets, J=2 Hz and 7 Hz, 1H); 7.60 (singlet, 1H); 7.73 (doublet, J=2 Hz, 1H); 8.25 (doublet, J=7 Hz, 1H); 13.45 (singlet, 1H).

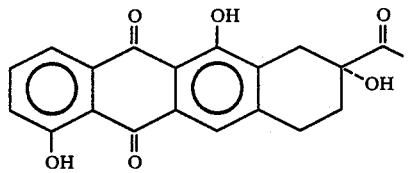

(±)-4-Demethoxy-6,7-dideoxy-4-hydroxydaunomycinone (±)-2-Acetyl-2,7,12-trihydroxy-1,2,3,4-tetrahydronaphthacene-6,11-dione Yield: 97%.
Melting point: 188°–190° C.
M.S.: m/z=352(6%), 334(20%), 309(100%), 291(24%), 280(20%), 279(23%), 266(32%).
I.R. (KBr disc): 3505 cm$^{-1}$, 2940, 2860, 1700, 1630, 1590, 1490, 1460, 1430, 1400, 1340, 1290, 1230, 1190, 1170, 1120, 1090, 1060, 1050, 965, 930, 915, 835, 815, 790, 730, 700.
NMR (CDCl$_3$): 2.39 (singlet, 3H); 3.08 (multiplet, 4H); 7.2–7.8 (multiplet, 4H); 12.70 (singlet, 1H); 13.09 (singlet, 1H).

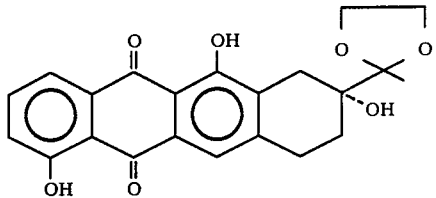

(±)-2-(1,1-Ethylenedioxyethyl)-2,7,12-trihydroxy-1,2,3,4-tetrahydronaphthacene-6,11-dione Yield: 98%.
Melting point: 216°–217° C.
M.S.: m/z=396(0.5%), 308(85%), 266(100%).
I.R. (KBr disc): 3440 cm$^{-1}$, 3000, 2950, 1640, 1600, 1570, 1480, 1460, 1430, 1400, 1380, 1360, 1320, 1310, 1280, 1260, 1200, 1170, 1100, 1090, 1080, 1060, 1040, 970, 955, 930, 910, 890, 850, 840, 800, 780, 730, 700, 650.
NMR (CDCl$_3$): 1.43 ppm (singlet, 3H); 2.0 (multiplet, 2H); 2.94 (multiplet, 4H); 4.08 (singlet, 4H); 7.5 multiplet, 4H); 12.73 (singlet, 1H); 13.08 (singlet, 1H).

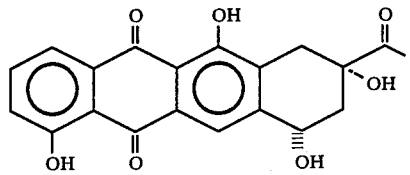

(±)-2-Acetyl-2α,4α,7,12-tetrahydroxy-1,2,3,4-tetrahydronaphthacene-6,11-dione (±)-4-Demethoxy-6-deoxy-4-hydroxydaunomycinone or (±)-6-deoxycarminomycinone Yield: 28%.
Melting point: 219°–221° C.
M.S.: m/z=368(8%), 350(19%), 332(32%), 307(78%), 279(100%).
I.R. (KBr disc): 3530 cm$^{-1}$, 3360, 2960, 2930, 1710, 1630, 1600, 1570, 1470, 1450, 1420, 1390, 1250, 1220, 1180, 1170, 1130, 1080, 1055, 1030, 950, 910, 900, 840, 790.
NMR (CDCl$_3$): 2.3 ppm (multiplet, 2H); 2.42 (singlet, 3H); 3.07 (singlet, 2H); 4.95 (multiplet, W$_{\frac{1}{2}}$=8.6 Hz, 1H); 7.25–8.04 (multiplet, 4H); 12.71 (singlet, 1H); 13.14 (1H).

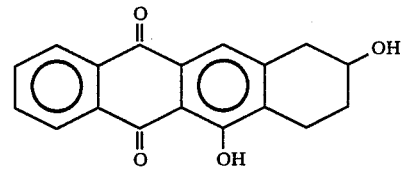

(±)-2,5-Dihydroxy-1,2,3,4-tetrahydronaphthacene-6,11-dione (±)-4-Demethoxy-9-deacetyl-7,11-deoxydaunomycinone Yield: 98%.

Melting point: 283°-285° C.
M.S.: m/z=294, 276.
I.R. (KBr disc): 3400 cm$^{-1}$ (broad), 2960, 1660, 1630, 1590, 1570, 1470, 1410, 1380, 1360, 1330, 1320, 1270, 1250, 1200, 1160, 1090, 1060, 1050, 1000, 970, 920, 820, 800, 710.

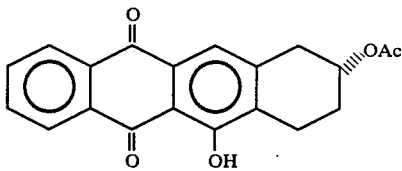

(±)-2-Acetoxy-5-hydroxy-1,2,3,4-tetrahydronaphtha-cene-6,11-dione (±)-9-O-Acetyl-4-demethoxy-9-deacetyl-7,11-deoxydaunomycinone Yield: 80%.
Melting point: 205°-206° C.
M.S.: m/z=336(7%); 276(100%).
I.R. (KBr disc): 3440 cm$^{-1}$ (broad), 2975, 1730, 1670, 1625, 1590, 1570, 1480, 1430, 1410, 1380, 1370, 1350, 1290, 1280, 1250, 1220, 1060, 1040, 970, 930, 790, 750, 725.
NMR (CDCl$_3$): 2.0 ppm (multiplet, 2H); 2.07 (singlet, 3H); 2.9 (multiplet, 4H); 5.23 (broad triplet, W$_{\frac{1}{2}}$=13 Hz, 1H); 7.4 (singlet, 1H); 7.7 (multiplet, 2H); 8.15 (multiplet, 2H); 12.8 (singlet, 1H).

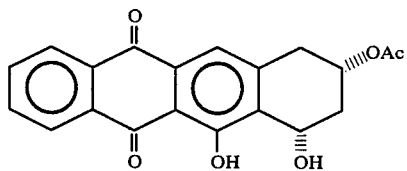

(±)-2α-Acetoxy-4α,5-dihydroxy-1,2,3,4-tetrahydronaphthacene-6,11-dione (±)-9-O-Acetyl-4-demethoxy-9-deacetyl-11-deoxydaunomycinone Yield: 28%.
Melting point: 182°-183° C.
M.S.: m/z=352(1.5%), 292(60%), 274(100%).
I.R. (KBr disc): 3500 cm$^{-1}$, 2980, 2960, 1730, 1670, 1630, 1590, 1520, 1480, 1430, 1420, 1390, 1370, 1290, 1270, 1250, 1060, 1030, 970, 800, 790, 720.
NMR (CDCl$_3$): 2.07 ppm (singlet, 3H); 2.33 (multiplet, 2H); (doublet, J=4 Hz, 1H); 3.67 (doublet, J=4 Hz, 1H); 5.23 (multiplet, W$_{\frac{1}{2}}$=16 Hz, 2H); 7.5 (singlet, 1H); 7.8 (multiplet, 2H); 8.23 (multiplet, 2H); 13.2 (singlet, 1H).

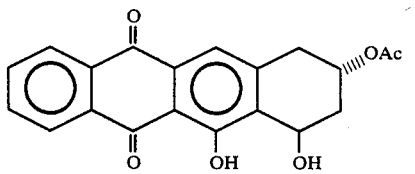

(±)-2-Acetoxy-4,5-dihydroxy-1,2,3,4-tetrahydronaphthacene-6,11-dione (±)-7-Epi-9-O-acetyl-4-demethoxy-9-deacetyl-11-deoxydaunomycinone Yield: 49%.
Melting point: 222°-227° C. (decomposition).
M.S.: m/z=352(1%), 292(18%), 274(100%).
I.R. (KBr disc): 2980, 2960, 1720, 1670, 1630, 1590, 1570, 1480, 1450, 1420, 1390, 1365, 1355, 1330, 1290, 1280, 1250, 1240, 1100, 1070, 1060, 1040, 980, 950, 910, 830, 790, 730.
NMR (CDCl$_3$): 2.07 ppm (singlet, 3H); 5.36 (multiplet, W$_{\frac{1}{2}}$=11.5 Hz, 2H); 7.59 (singlet, 1H); 7.80 (multiplet, 2H); 8.25 (multiplet, 2H); 13.37 (singlet, 1H).

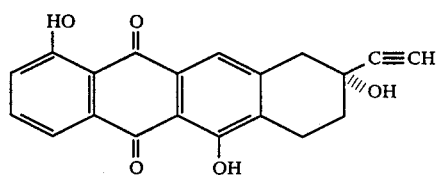

(±)-2-Ethynyl-2,5,10-trihydroxyl-1,2,3,4-tetrahydronaphthacene-6,11-dione

Yield: 60%.
Melting point: 225°-226° C.
I.R. (CH$_2$Cl$_2$): 3420 cm$^{-1}$, 3300, 2960, 2940, 1640, 1610, 1580, 1485, 1475, 1460, 1430, 1395, 1340, 1320, 1270, 1205, 1195, 1165, 1150, 1095, 1060, 1050, 1030, 1000, 960, 915, 840, 780.
M.S.: m/z=334(12%), 333(54%), 316(45%), 307(55%), 280(39%), 266(100%).

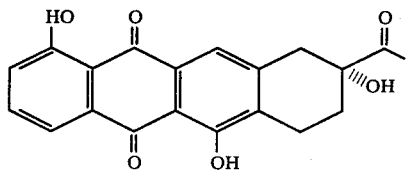

(±)-2-Acetyl-2,5,10-trihydroxy-1,2,3,4-tetrahydronaphthacene-6,11-dione

Yield: quantitative.
Melting point: 226°-228° C.
M.S.: m/z=352(26%), 309(100%), 291(42%), 279(37%), 266(18%), 205(24%), 189(24%), 164(22%), 152(25%), 121(53%), 115(41%), 93(46%), 91(46).
I.R. (KBr): 3460 cm$^{-1}$, 2920, 1860, 1705, 1635, 1625, 1615, 1610, 1600, 1580, 1570, 1470, 1450, 1410, 1395, 1365, 1335, 1280, 1270, 1190, 1160, 1090, 1050, 970, 950, 905, 800, 785, 710.

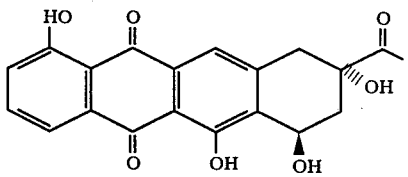

(±)-2-Acetyl-2α,4β,5,10-tetrahydroxy-1,2,3,4-tetrahydronaphthacene-6,11-dione

Melting point: 209°–211° C.

I.R. (KBr): 3500 cm⁻, 3350, 2940, 1695, 1615, 1610, 1580, 1475, 1455, 1420, 1395, 1375, 1340, 1320, 1275, 1245, 1210, 1160, 1120, 1090, 1080, 1060, 1030, 975, 940, 905, 900, 840, 810, 800, 730, 695.

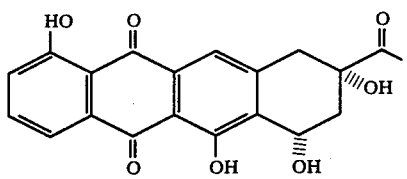

(±)-2-Acetyl-2α,4α,10-trihydroxy-1,2,3,4-tetrahydronaphthacene-6,11-dione

=4-Demethoxy-11-deoxy-1-hydroxydaunomycionone

Melting point: 209°–211° C.

M.S.: m/z=368(11%), 332(14%), 317(11%), 307(29%), 279(18%), 205(10%), 131(32%), 119(42%), 106(69%), 105(100%).

I.R. (KBr): 3580 cm⁻¹, 3520, 3490, 2930, 2860, 1720, 1635, 1620, 1590, 1490, 1470, 1435, 1400, 1385, 1350, 1290, 1275, 1220, 1175, 1125, 1120, 1080, 1070, 1040, 930, 815.

What is claimed is:

1. Aglycon compounds corresponding to the general formula IV below:

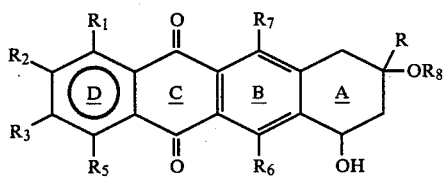

in which:

$R_1$, $R_2$, $R_3$, and $R_5$, which can be identical or different, represent a hydrogen atom or a group OH, OMetal or $OR_4$, $R_4$ being a substituted or unsubstituted $C_1$ to $C_6$ alkyl group, R represents a hydrogen atom or a group $COCH_2R'$, $R'$ being hydrogen or an alkyl, hydroxyl, alkoxy or aryl group, $R_6$ and $R_7$, which are always different, represent either a hydrogen atom or an OH group, and $R_8$, which is located on the A ring in the compound of formula IV, represents a hydrogen atom or the group $CH_3CO-$, with the proviso that:

(a) $R_1$, $R_2$ and $R_3$ are never simultaneously hydrogen when $R_7$ and $R_8$ represent the hydrogen atom and R is the group $COCH_2R'$, and (b) if $R_1$, $R_2$, $R_3$ and $R_6$ are hydrogen, $R_5$ is other than hydrogen and $OCH_3$.

2. An aglycon as claimed in claim 1, wherein the two OH groups of the A ring are in the cis position relative to one another.

3. An aglycon as claimed in claim 1, wherein the two OH groups of the A ring are in the trans position relative to one another.

4. An aglycon as claimed in claim 1, which is an 11-deoxyaglycon.

5. An aglycon as claimed in claim 1, which is a 6-deoxyaglycon.

6. An aglycon as claimed in claim 1, which is an 11-deoxyaglycon and which is taken from the group comprising:

the aglycon in which $R_1=OH$; $R_2=R_3=R_5=H$; $R_6=OH$; $R=COCH_3$; $R_8=H$, the aglycon in which $R_1=R_3=R_5=H$; $R_2=OCH_3$; $R_6=OH$; $R=COCH_3$; $R_8=H$, the aglycon in which $R_1=R_2=R_5=H$; $R_3=OCH_3$; $R_6=OH$; $R=COCH_3$; $R_8=H$ and the aglycon in which $R_1=R_2=R_3=R_5=R=H$; $R_6=OH$; $R_8=COCH_3$.

7. An aglycon as claimed in claim 1, which is a 6-deoxyaglycon and which corresponds to the product in which: $R_1=R_2=R_3=R_6=H$; $R_7=OH$; $R_5=OH$; $R=COCH_3$.

* * * * *